United States Patent [19]

Ishikawa et al.

[11] 4,383,027

[45] May 10, 1983

[54] SILVER HALIDE COLOR PHOTOGRAPHIC LIGHT-SENSITIVE MATERIAL AND METHOD FOR DEVELOPING THEREOF

[75] Inventors: Takatoshi Ishikawa; Masakazu Morigaki; Takashi Nakamura; Nobuo Furutate, all of Kanagawa, Japan

[73] Assignee: Fuji Photo Film Co., Ltd., Minami-ashigara, Japan

[21] Appl. No.: 391,331

[22] Filed: Jun. 23, 1982

[30] Foreign Application Priority Data

Jun. 23, 1981 [JP] Japan .................................. 56-97255

[51] Int. Cl.³ .................................................. G03C 1/40
[52] U.S. Cl. ..................... 430/372; 430/387; 430/504; 430/505; 430/551; 430/555; 430/558
[58] Field of Search ............... 430/372, 387, 551, 555, 430/558, 504, 505

[56] References Cited

U.S. PATENT DOCUMENTS

| | | | |
|---|---|---|---|
| 2,579,436 | 12/1951 | Mackey | 430/372 |
| 2,688,024 | 8/1954 | Kendall et al. | 430/483 |
| 4,179,293 | 12/1979 | Hirano et al. | 430/551 |
| 4,268,621 | 5/1981 | Ogi et al. | 430/551 |
| 4,310,623 | 1/1982 | Watanabe et al. | 430/551 |
| 4,351,897 | 9/1982 | Aoki et al. | 430/555 |

*Primary Examiner*—J. Travis Brown

*Attorney, Agent, or Firm*—Sughrue, Mion, Zinn, Macpeak and Seas

[57] ABSTRACT

A silver halide color photographic light-sensitive material comprising a support having thereon a silver halide emulsion layer containing at least one coupler represented by the following general formula (I):

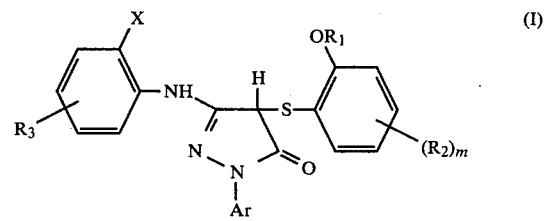

The substituents are disclosed in the specification. The silver halide color photographic light-sensitive material in which a specific class of 1-phenyl-3-anilono-4-phyenylthio-5-pyrazolone type two-equivalent magenta color image forming couplers and a specific class of 1-phenyl-3-pyrazolidone derivatives are used in association with each other can provide a magenta color image of high sensitivity without increasing the fog level. A method for developing the material is also disclosed.

22 Claims, No Drawings

SILVER HALIDE COLOR PHOTOGRAPHIC LIGHT-SENSITIVE MATERIAL AND METHOD FOR DEVELOPING THEREOF

FIELD OF THE INVENTION

The present invention relates to a color photographic light-sensitive material, and more particularly to a color photographic light-sensitive material wherein color forming sensitivity in a magenta color image forming layer is high and color fog is low.

BACKGROUND OF THE INVENTION

It is known that when a silver halide colour photographic material is colour-developed, a coupler reacts with an oxidized aromatic primary amine colour developing agent to provide an indophenol, indoaniline, indamine, azomethine, phenoxazine, phenazine or other similar dye, whereby a colour image is formed. In such a system, colour reproduction is conventionally conducted by the subtractive colour process and silver halide emulsions, which are selectively sensitive to blue, green and red light, respectively, and the corresponding yellow, magenta and cyan dye image forming couplers are used. To form a yellow dye image, an acylacetanilide or dibenzoylmethane coupler is usually used, to form a magenta dye image, a pyrazolone, a pyrazolobenzimidazol a cyano-acetophenone, or indazolone coupler is used, and to form a cyan dye image, a phenolic coupler such as a phenol or a naphthol is used.

Most conventional dye image forming couplers are four-equivalent couplers, i.e. they theoretically require development of four moles of exposed silver halide as an oxidizing agent to form one mole of dye by coupling. On the other hand, two-equivalent couplers, which have an active methylene group substituted with a group which is released when the coupler couples with an oxidized aromatic primary amine colour developing agent, require only development of two moles of exposed silver halide to form one mole of dye. Since two-equivalent couplers require only half the amount of silver halide to form a dye as compared with four-equivalent couplers, two-equivalent couplers have many advantages, for example, a decrease in the processing time of the light-sensitive materials and improvements in the photographic properties and reduction in costs due to a decrease in the thickness of the emulsion layers.

Several attempts have been made to provide two-equivalent couplers by modifying 5-pyrazolone couplers which have been conventionally employed as magenta dye-forming couplers. For instance, the 4-position of a 5-pyrazolone coupler can be substituted with a thiocyano group as described in U.S. Pat. Nos. 3,214,437 and 3,253,924, an acyloxy group as described in U.S. Pat. No. 3,311,476, an aryloxy group as described in U.S. Pat. No. 3,419,391, a 2-triazolyl group as described in U.S. Pat. No. 3,617,291 or a halogen atom as described in U.S. Pat. No. 3,522,052.

However, the use of these 4-substituted-5-pyrazolone couplers is accompanied by various disadvantages, namely that a marked colour fog is produced, the coupling reactivity is insufficient, the couplers are unstable and their coupling reactivities are lost in the light-sensitive materials during storage, or the preparation of the couplers is quite difficult.

The 5-pyrazolones in which the 4-position is substituted with an alkylthio group, an arylthio group or a heterocyclic thio group are also known, as described in U.S. Pat. No. 3,227,554. However, most of these known thio-substituted pyrazolone compounds have insufficient coupling reactivity with an oxidation product of a aromatic primary amine colour developing agent, and are difficult to use them in conventional colour photographic light-sensitive materials due to the adverse effects on photographic properties of the mercapto compounds which are formed as a result of the coupling reaction. Furthermore, the chemical stabilities of these couplers are insufficient.

The color forming sensitivity of the above described two-equivalent magenta couplers is not necessarily sufficient for increasing the sensitivity of color photographic light-sensitive material which is the latest technical subject. Therefore, it has been strongly desired to develop a technique for increasing the sensitivity of a magenta color image forming layer.

Recently, the knowledge that magenta couplers having an alkylthio coupling-off group have a particularly high activity and a high color forming sensitivity has been obtained as described in Japanese Patent Application (OPI) No. 62454/80 or U.S. Pat. No. 4,264,723. However, these couplers are still insufficient for obtaining highly sensitive color photographic light-sensitive materials. ("OPI" refers to "open to public inspection")

In order to further improve these properties, magenta couplers having an arylthio coupling-off group are developed as described in Japanese Patent Application (OPI) No. 35858/82 or U.S. patent application Ser. No. 291,886 and a technique of using a diffusion-resistant 1-phenyl-3-pyrazolidone derivative together with the above-described magenta coupler for the purpose of preventing the formation of magenta fog during color development is conceived. As a result, it becomes possible to obtain properties which are sufficient for practical use.

SUMMARY OF THE INVENTION

An object of the present invention is to provide a color photographic light-sensitive material having high color forming sensitivity, a reduced amount of coated silver and a low level of fog in a magenta color image forming layer and a method for developing thereof.

Other objects of the present invention will become apparent from the following detailed description and examples.

The above-described objects of the present invention can be attained by a silver halide color photographic light-sensitive material comprising a support having thereon a silver halide emulsion layer containing at least one coupler represented by the following general formula (I):

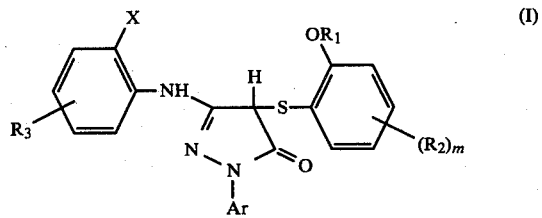

wherein $R_1$ represents an alkyl group or an aryl group 1; $R_2$ represents a hydrogen atom, hydroxy group, a halogen atom, an alkyl group, an alkoxy group or an aryl group; $R_3$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trichloromethyl group; X represents a halogen atom or an alkoxy group; Ar represents a substituted phenyl group; m is an integer of from 1 to 4; and the above described organic residues may be substituted; and the silver halide emulsion layer and/or a hydrophilic colloid layer adjacent thereto containing a 1-phenyl-3-pyrazolidone derivative represented by the following general formula (II):

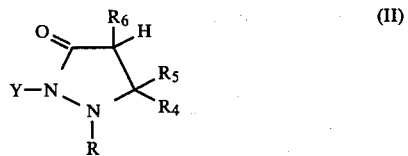

(II)

wherein Y represents a hydrogen atom or an acyl group; R and $R_4$, which may be the same or different, each represents an aryl group; $R_5$ represents a hydrogen atom or an alkyl group; $R_6$ represents a hydrogen atom, an alkyl group or an aryl group; and the above described organic residues may be substituted. A method of forming a color image by color development thereof is also disclosed.

DETAILED DESCRIPTION OF THE INVENTION

The magenta couplers of the general formula (I) are described in more detail below.

In the general formula (I), Ar is a substituted phenyl group. The substituent for the phenyl group includes a halogen atom (for example, a chlorine atom, a bromine atom, a fluorine atom, etc.), an alkyl group having from 1 to 22 carbon atoms (for example, a methyl group, an ethyl group, a tetradecyl group, a tert-butyl group, etc.), an alkoxy group having from 1 to 22 carbon atoms (for example, a methoxy group, an ethoxy group, an octyloxy group, a dodecyloxy group, etc.), an alkoxycarbonyl group having from 2 to 23 carbon atoms (for example, a methoxycarbonyl group, an ethoxycarbonyl group, a tetradecyloxycarbonyl group, etc.), or a cyano group. A number of the substituents may be from 1 to 5.

X in the general formula (I) represents a halogen atom (for example, a chlorine atom, a bromine atom, a fluorine atom, etc.) or an alkoxy group having from 1 to 22 carbon atoms (for example, a methoxy group, an octyloxy group, a dodecyloxy group, etc.).

$R_3$ in the general formula (I) represents a hydrogen atom, a halogen atom (for example, a chlorine atom, a bromine atom, a fluorine atom, etc.), a substituted or unsubstituted straight chain or branched chain alkyl group (for example, a methyl group, a tert-butyl group, a tetradecyl group, etc.), a substituted or unsubstituted alkoxy group (for example, a methoxy group, an ethoxy group, a 2-ethylhexyloxy group, a tetradecyloxy group, etc.), a substituted or unsubstituted acrylamino group (for example, an acetamido group, a benzamido group, butanamido group, a tetradecanamido group, an α-(2,4-di-tert-amylphenoxy)-acetamido group, an α-(2,4-di-tert-amylphoenoxy)butyramido group, an α-(3-pentadecylphenoxy)hexanamido group, an α-(4-hydroxy-3-tert-butylphenoxy)tetradecanamido group, a 2-oxopyrrolidin-1-yl group, a 2-oxo-5-tetradecylpyrrolidin-1-yl group, an N-methyltetradecanamido group, etc.), an alkane or aromatic hydrocarbon sulfonamido group or an N-substituted sulfonamido group (for example, a methanesulfonamido group, a benzenesulfonamido group, a p-toluenesulfonamido group, an octanesulfonamido group, a p-dodecylbenzenesulfonamido group, an N-methyltetradecanesulfonamido group, etc.), a sulfamoyl group or an N-substituted sulfamoyl group (for example, an N-methylsulfamoyl group, an N-hexadecylsulfamoyl group, an N-[3-(dodecyloxy)-propyl]sulfamoyl group, an N-[4-(2,4-di-tert-amylphenoxy)butyl]sulfamoyl group, an N-methyl-N-tetradecylsulfamoyl group, etc.), a carbamoyl group or an N-substituted carbamoyl group (for example, an N-methylcarbamoyl group, an N-octadecylcarbamoyl group, an N-[4-(2,4-di-tert-amylphenoxy)butyl]carbamoyl group, an N-methyl-N-tetradecylcarbamoyl group, etc.), a diacylamino group (for example, an N-succinimido group, an N-phthalimido group, a 2,5-dioxo-1-oxazolidinyl group, a 3-dodecyl-2,5-dioxo-1-hydantoinyl group, a 3-(N-acetyl-N-dodecylamino)succinimido group, etc.), a substituted or unsubstituted alkoxycarbonyl group (for example, a methoxycarbonyl group, a tetradecyloxycarbonyl group, a benzyloxycarbonyl group, etc.), an alkoxysulfonyl group (for example, a methoxysulfonyl group, an octyloxysulfonyl group, a tetradecyloxysulfonyl group, etc.), an aryloxysulfonyl group (for example, a phenoxysulfonyl group, a 2,4-di-tert-amylphenoxysulfonyl group, etc.), an alkanesulfonyl group (for example, a methanesulfonyl group, an octanesulfonyl group, a 2-ethylhexanesulfonyl group, a hexadecanesulfonyl group, etc.), an arylsulfonyl group (for example, a benzenesulfonyl group, a 4-nonylbenzenesulfonyl group, etc.), a substituted or unsubstituted alkylthio group (for example, an ethylthio group, a hexylthio group, a benzylthio group, a tetradecylthio group, a 2-(2,4-di-tert-amylphenoxy)ethylthio group, etc.), an arylthio group (for example, a phenylthio group, a p-tolythio group, etc.) a substituted or unsubstituted alkyloxycarbonylamino group (for example, an ethyloxycarbonylamino group, a benzyloxycarbonylamino group, a hexadecyloxycarbonylamino group, etc.), an alkylureido group (for example, an N-methylureido group, an N,N-dimethylureido group, an N-methyl-N-dodecylureido group, an N-hexadecylureido group, an N,N-dioctadecylureido group, etc.), a substituted or unsubstituted acyl group (for example, an acetyl group, a benzoyl group, an octadecanoyl group, a p-dodecanamidobenzoyl group, etc.), a nitro group, a carboxy group or a trichloromethyl group. In the above-described substituents, the alkyl moieties thereof preferably have from 1 to 36 carbon atoms, and the aryl moieties thereof preferably have from 6 to 38 carbon atoms.

$R_1$ in the general formula (I) represents a substituted or unsubstituted alkyl group having from 1 to 22 carbon atoms (for example, a methyl group, a propyl group, a butyl group, a 2-methoxyethyl group, a methoxymethyl group, a hexyl group, a 2-ethylhexyl group, a dodecyl group, a hexadecyl group, a 2-(2,4-di-tert-amylphenoxy)ethyl group, a 2-dodecyloxyethyl group, etc.) or a substituted or unsubstituted aryl group having from 6 to 18 carbon atoms (for example, a phenyl group, an α- or β-naphthyl group, a 4-tolyl group, etc.).

$R_2$ in the general formula (I) represents a hydrogen atom, a hydroxy group, or a halogen atom, an alkyl group, an alkoxy group, or an aryl group, each as defined for $R^3$-above.

Of the couplers represented by the general formula (I) those in which the total number of carbon atoms included in the groups represented by $R_1$ and $R_2$ is not less than 6 are particularly preferred for achieving the objects of the present invention.

Specific examples of the typical couplers according to the present invention are set forth below, but the present invention is not to be construed as being limited to these compounds. In the following formulae, the alkyl groups mean normal alkyl groups unless otherwise indicated.

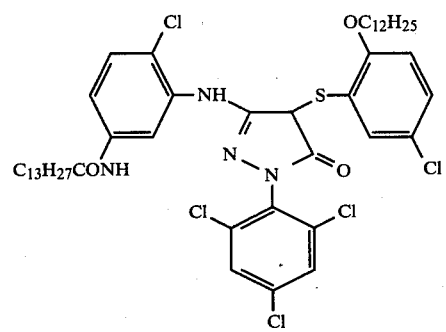

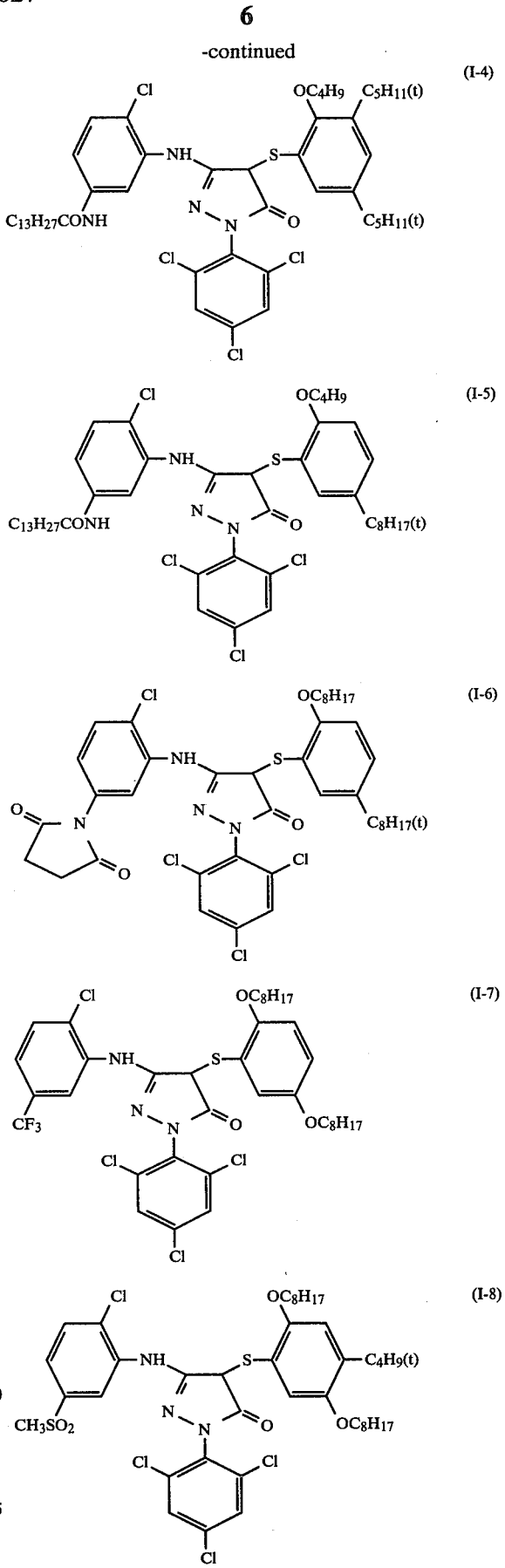

-continued
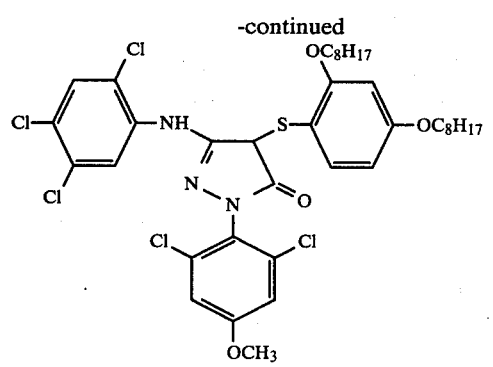 (I-9)
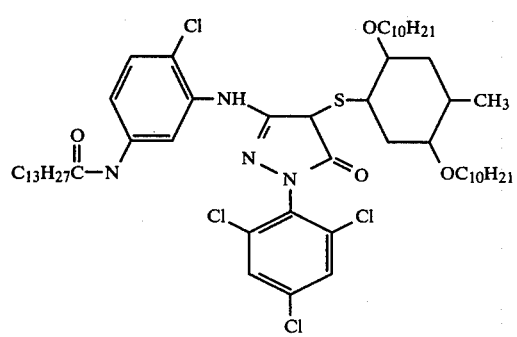 (I-10)
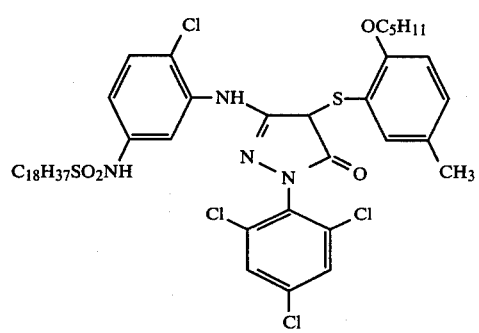 (I-11)
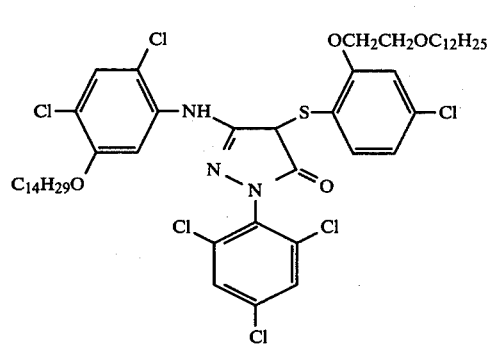 (I-12)
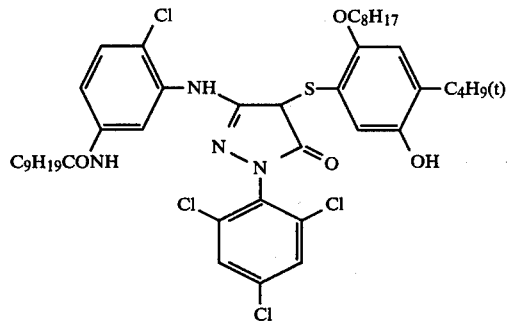 (I-13)
-continued
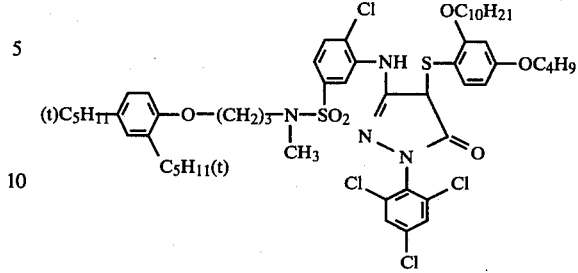 (I-14)
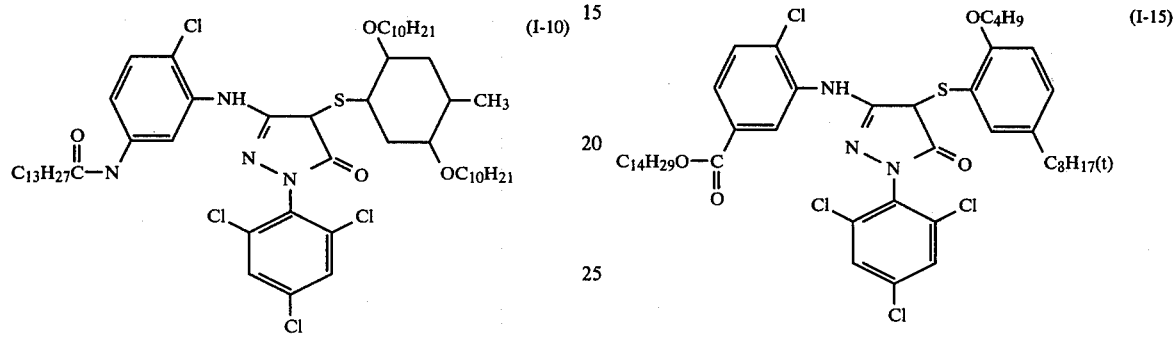 (I-15)
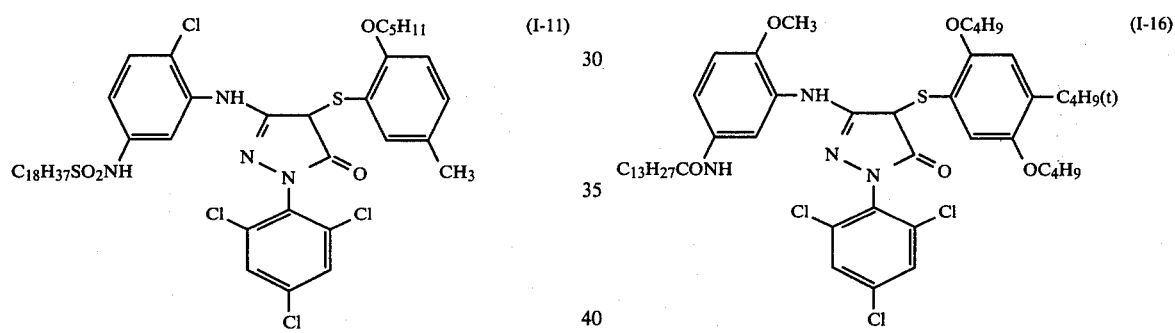 (I-16)
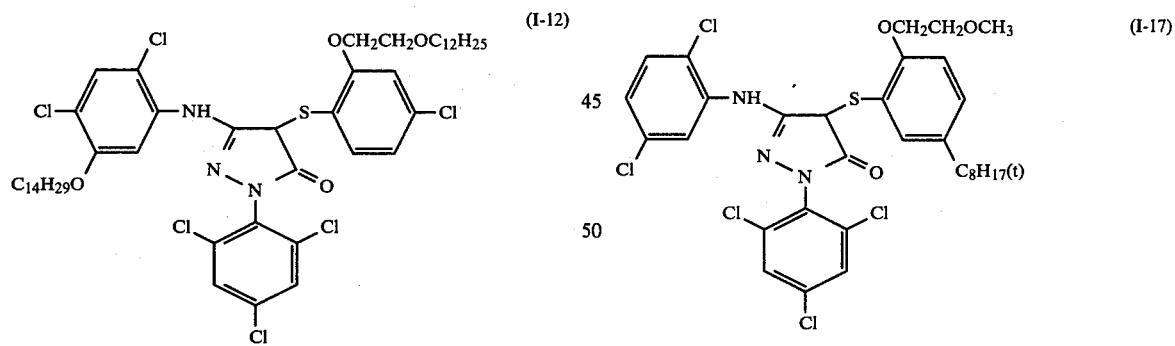 (I-17)
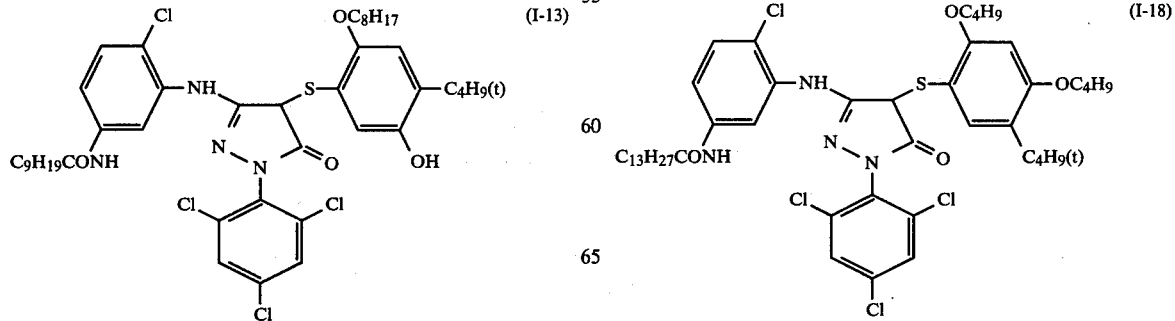 (I-18)

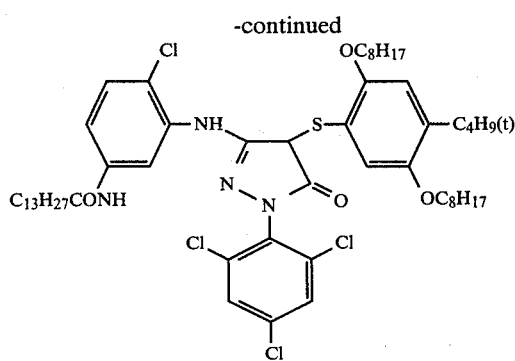 (I-19)
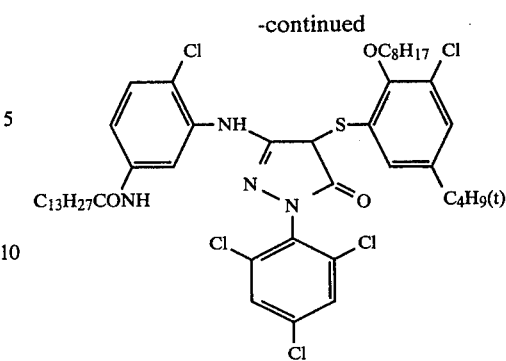 (I-24)
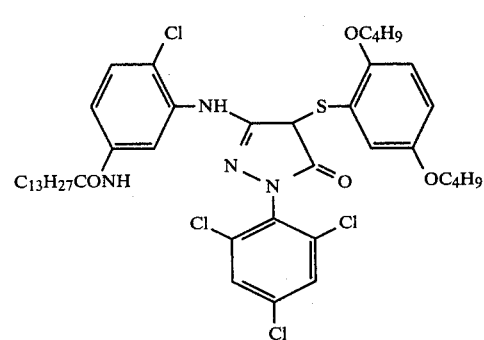 (I-20)
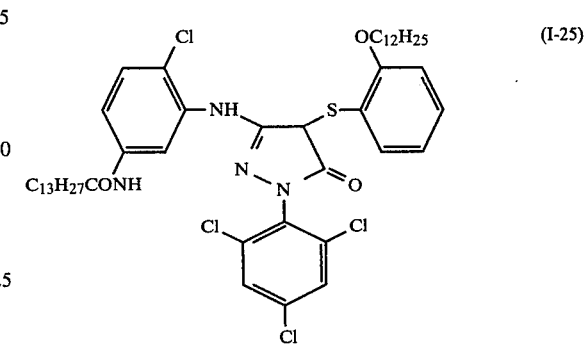 (I-25)
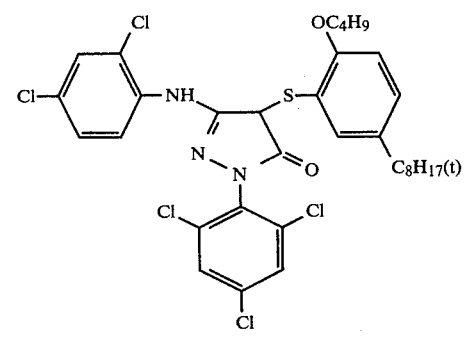 (I-21)
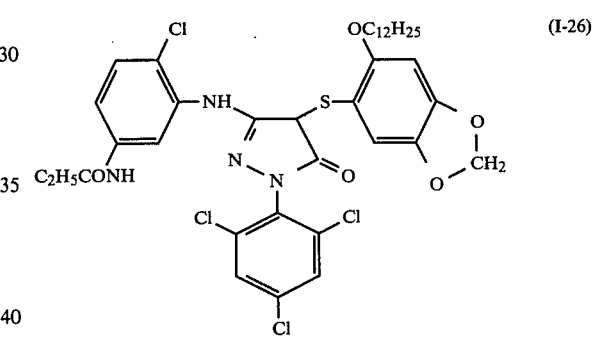 (I-26)
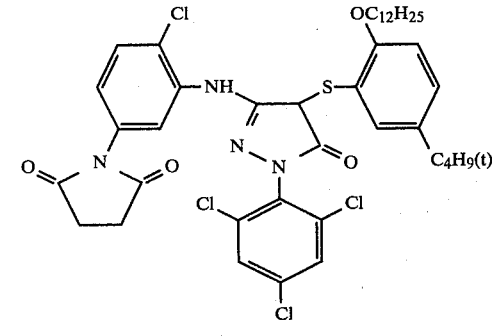 (I-22)
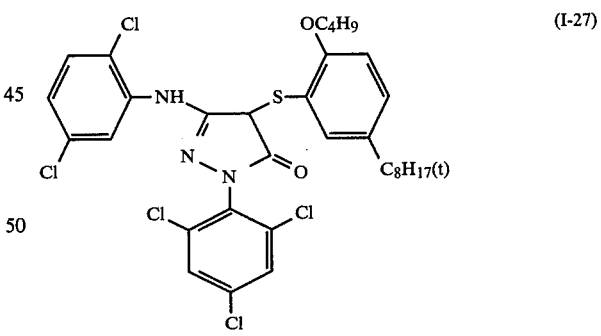 (I-27)
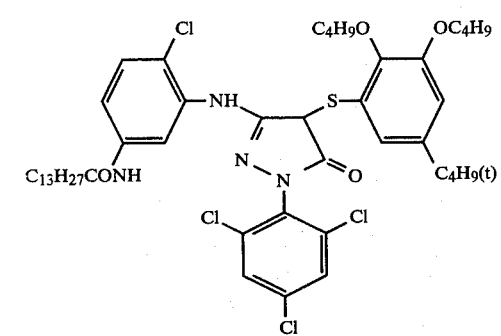 (I-23)
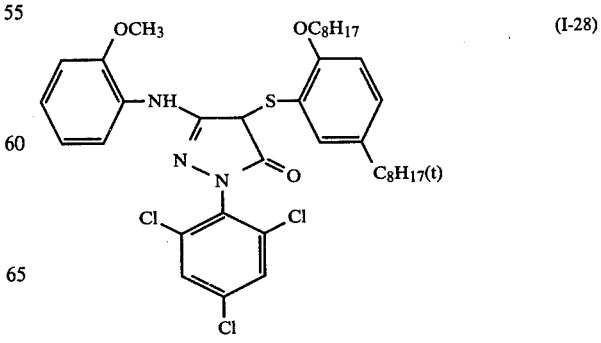 (I-28)

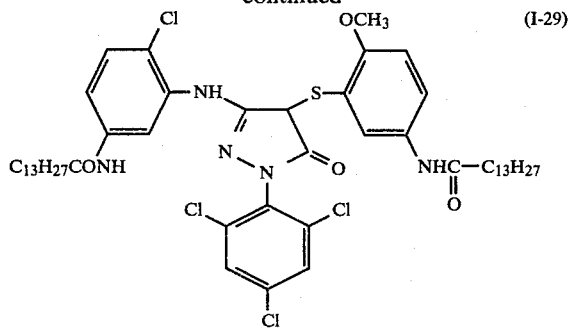
(I-29)

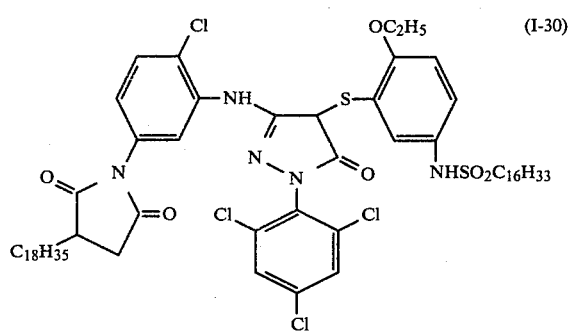
(I-30)

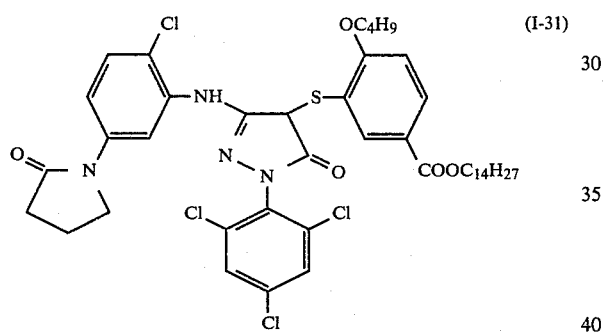
(I-31)

The magenta couplers which can be used in the present invention can be synthesiged using a corresponding thiophenol derivative which forms a coupling releasable group and the so-called four-equivalent coupler in which the coupling active position is not substituted by the method as described in Japanese Patent Application (OPI) No. 35858/82 or U.S. Patent Application Ser. No. 291,886.

The compounds represented by the general formula (II) are described in more detail below.

In the general formula (II), Y represents a hydrogen atom an aliphatic acyl group having from 2 to 15 carbon atoms or an aromatic acyl group having from 6–15 carbon atoms (for example, an acetyl group, etc.).

R and $R_4$ in the general formula (II) each represents a substituted or unsubstituted aryl group having from 6 to 30 carbon atoms (for example, a phenyl group, a 4-methylphenyl group, a 3-ethylphenyl group, a 4-tert-butylphenyl group, a 4-chlorophenyl group, a 4-methoxyphenyl group, a 3-methoxyphenyl group, a 2-hydroxyphenyl group, a 4-acetylaminophenyl group, a 3-chloro-4-methylphenyl group, a 3-(ethylthioethoxy)-phenyl group, a 3-(dimethylaminoethoxy)phenyl group, $-C_6H_4OCH_2CH_2N(CH_3)_3^+ \cdot Cl^-$, etc.).

$R_5$ in the general formula (II) represents a hydrogen atom, an alkyl group having from 1 to 12 carbon atoms (for example, a methyl group, an ethyl group, an isopropyl group, a cyclohexyl group, etc.).

$R_6$ in the general formula (II) represents a hydrogen atom, a substituted or unsubstituted alkyl group having from 1 to 10 carbon atoms (for example, a methyl group, an ethyl group, an isopropyl group, a tert-butyl group, a cyclohexyl group, a hydroxymethyl group, etc.) or a substituted or unsubstituted aryl group having from 6 to 30 carbon atoms (for example, a phenyl group, a 4-methylphenyl group, a 3-methoxyphenyl group, a 4-chloro-3-hydroxyphenyl group, etc.).

Specific examples of the compounds represented by the general formula (II) are set forth below, but the present invention is not to be construed as being limited to these compounds.

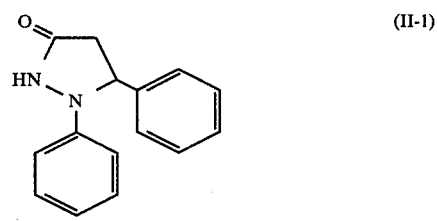
(II-1)

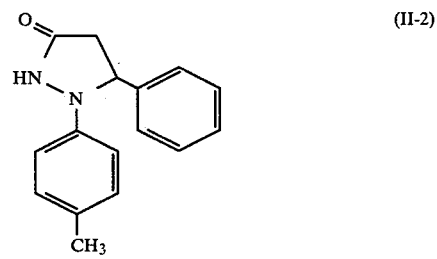
(II-2)

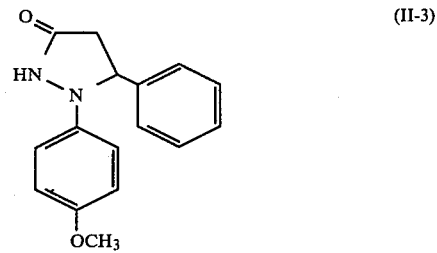
(II-3)

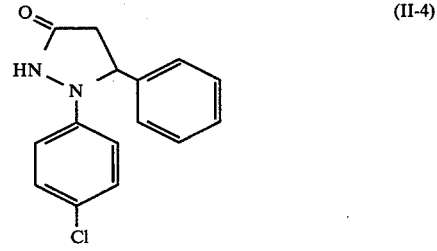
(II-4)

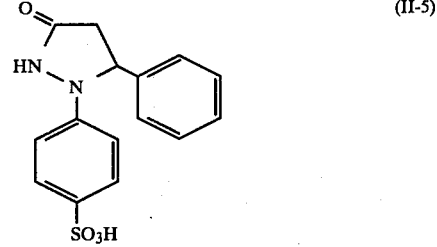
(II-5)

-continued
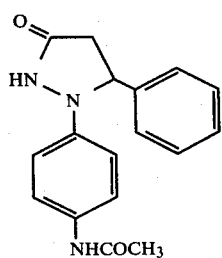 (II-6)
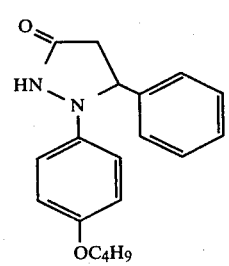 (II-7)
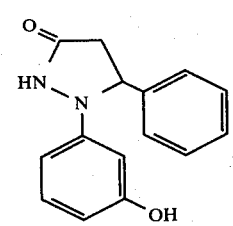 (II-8)
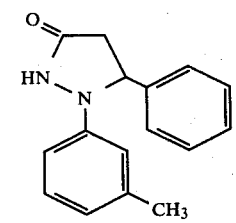 (II-9)
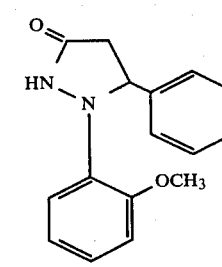 (II-10)
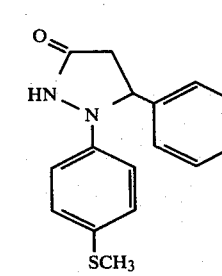 (II-11)
-continued
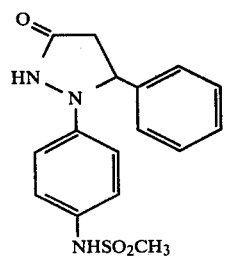 (II-12)
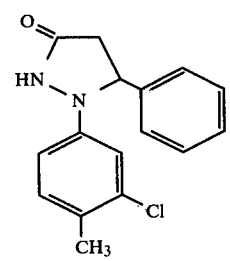 (II-13)
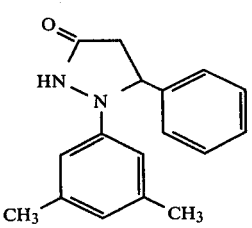 (II-14)
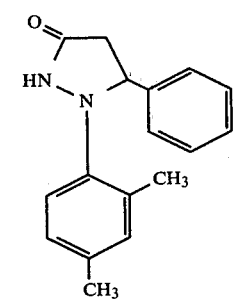 (II-15)
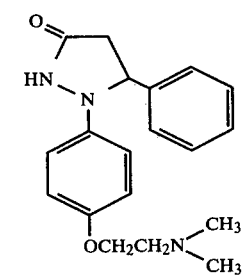 (II-16)
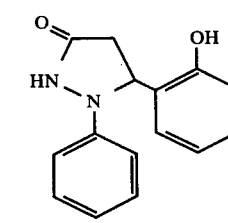 (II-17)

-continued
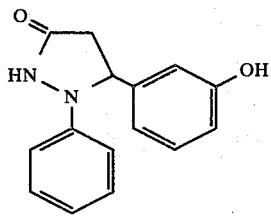 (II-18)
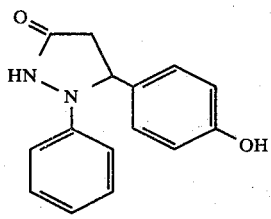 (II-19)
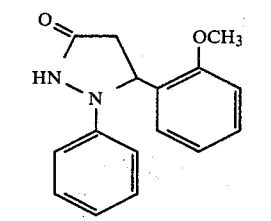 (II-20)
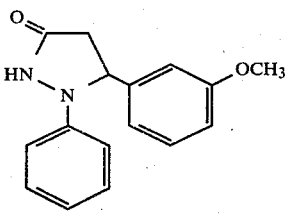 (II-21)
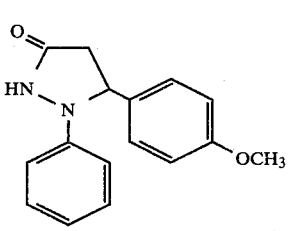 (II-22)
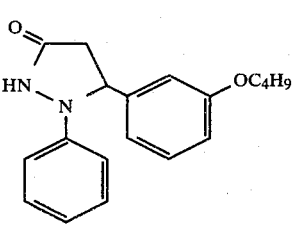 (II-23)
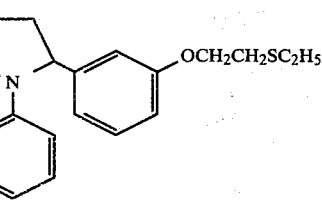 (II-24)
-continued
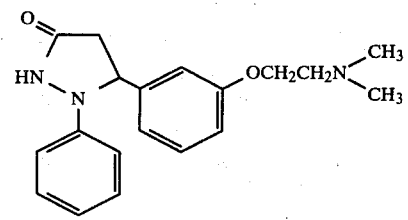 (II-25)
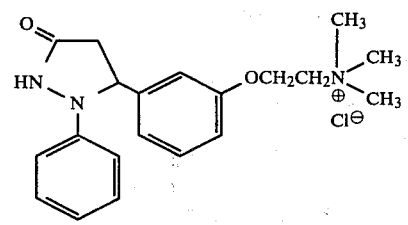 (II-26)
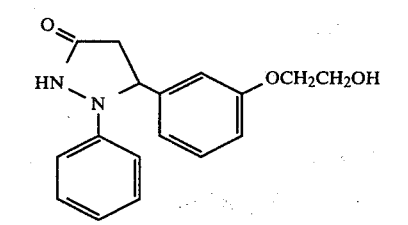 (II-27)
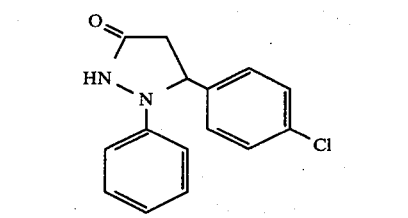 (II-28)
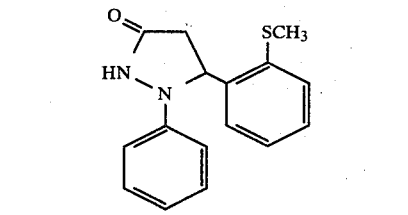 (II-29)
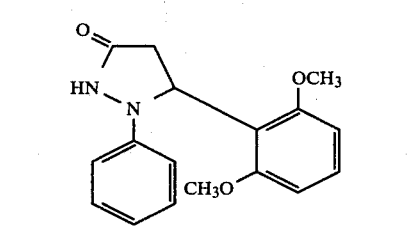 (II-30)
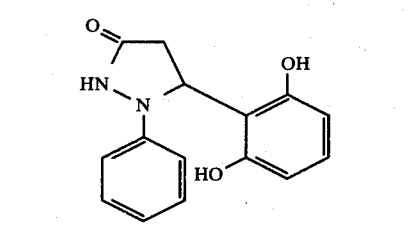 (II-31)

-continued
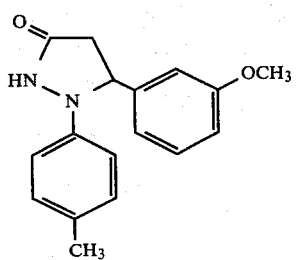 (II-32)
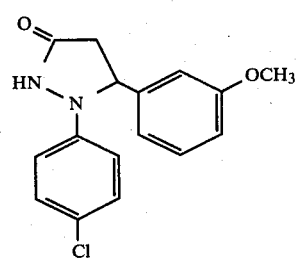 (II-33)
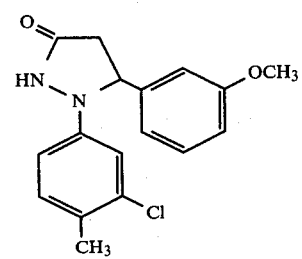 (II-34)
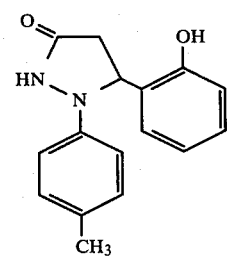 (II-35)
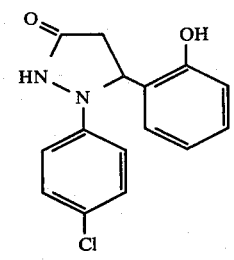 (II-36)
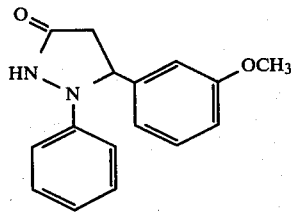 (II-37)
-continued
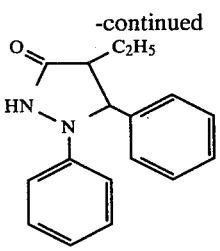 (II-38)
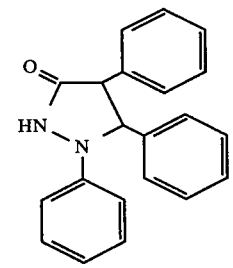 (II-39)
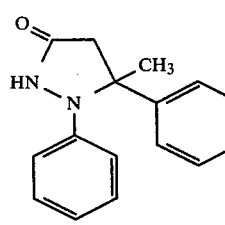 (II-40)
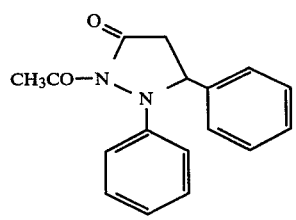 (II-41)
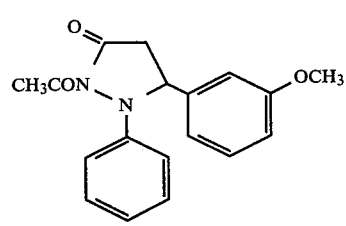 (II-42)
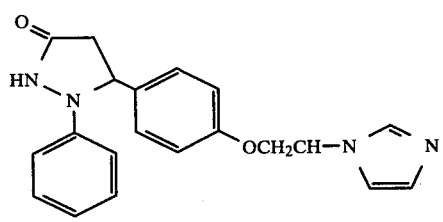 (II-43)
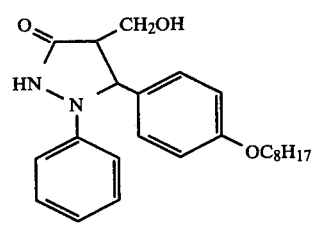 (II-44)

In the present invention, the compound represented by the general formula (I) is generally used from $1 \times 10^{-5}$ to $1 \times 10^{-2}$ mol/m$^2$, preferably from $1 \times 10^{-4}$ to $1 \times 10^{-3}$ mol/m$^2$ in the silver halide emulsion layer. The compound represented by the general formula (II) is generally used from $1 \times 10^{-6}$ to $1 \times 10^{-2}$ mol/m$^2$, preferably from $1 \times 10^{-5}$ to $1 \times 10^{-3}$ mol/m$^2$ in the silver halide emulsion layer or in the hydrophilic colloid layer. The amount of Ag in the emulsion layer is generally 0.1 to 10 g/m$^2$, preferably 0.2 to 1.0 g/m$^2$. The amount of the compound represented by the general formula (II) is from preferably $1 \times 10^{-3}$ to 1 mole per mole of silver in the silver halide emulsion layer.

The compounds represented by the general formula (II) in the present invention can be synthesized with reference to the methods as described in U.S. Pat. Nos. 2,688,024 and 2,704,762. Synthesis examples of specific compounds are shown below.

SYNTHESIS EXAMPLE 1

Synthesis of Compound II-2

A mixture solution composed of 22.2 g of 4-methylphenylhydrazine hydrochloride, 1.5 g of tert-butylhydroquione, 67.5 ml of methanol containing 28% of sodium methoxide and 250 ml of n-butanol was heated with stirring under nitrogen atmosphere and methanol was distilled off. Then, 29.6 g of ethyl cinnamate was added dropwise to the mixture over a period of 30 minutes and heated with stirring for 2 hours while distilling off n-butanol at an ambient pressure. The reaction solution was cooled, neutralized with an aqueous hydrochloric acid solution and extracted with ethyl acetate. The extracte was washed with water and dried with anhydrous magnesium sulfate. The solvent was distilled off and the residue was crystallized with ethyl acetate to obtain 7.7 g of compound II-2. The melting point was 156° to 158° C.

Elemental Analysis: Calculated for $C_{16}H_{16}N_2O$; C: 76.17%, H: 6.39%, N: 11.10%. Found; C: 76.20%, H: 6.19%, N: 11.07%.

SYNTHESIS EXAMPLE 2

Synthesis of Compound II-18

A mixture solution composed of 18 g of phenylhydrazine, 1.0 g of tert-butylhydroquinone, 50.2 ml of methanol containing 28% of sodium methoxide and 250 ml of n-butanol was heated with stirring under nitrogen atmosphere and methanol was distilled off. Then, 100 ml of an n-butanol solution containing 32 g of ethyl m-hydroxycinnamate was added dropwise to the mixture over a period of 30 minutes and heated with stirring for 3 hours while distilling off n-butanol at an ambient pressure. The reaction solution was cooled, neutralized with an aqueous hydrochloric acid solution and extracted with n-butanol. The extract was washed with a saturated aqueous sodium chloride solution and dried with anhydrous magnesium sulfate. The solvent was distilled off and the residue was recrystallized from a solvent mixture of methanol and n-hexane (2:1 in volume) to obtain 14.1 g of compound II-18. The melting point was 188° to 189.5° C.

Elemental Analysis: Calculated for $C_{15}H_{14}N_2O_2$; C: 70.85%, H: 5.55%, N:11.01%. Found; C: 70.84%, H: 5.43%, N:11.17%.

SYNTHESIS EXAMPLE 3

Synthesis of Compound II-21

A mixture solution composed of 19.4 g of phenylhydrazine, 1.6 g of tert-butylhydroquinone, 60.3 ml of methanol containing 28% of sodium methoxide and 250 ml of n-butanol was heated with stirring under nitrogen atmosphere and methanol was distilled off. Then, 100 ml of an n-butanol solution containing 41.2 g of ethyl m-methoxycinnamate was added dropwise to the mixture over a period of 30 minutes and heated with stirring for 1 hour while distilling off n-butanol at an ambient pressure. The reaction solution was cooled, neutralized with an aqueous hydrochloric acid solution and extracted with n-butanol. The extract was washed with a saturated aqueous sodium chloride solution and dried with anhydrous magnesium sulfate. The solvent was distilled off and the residual said was recrystallized from methanol to obtain 30 g of Compound II-21. The melting point was 164° to 166° C.

Elemental Analysis: Calculated for $C_{16}H_{16}N_2O_2$; C: 71.62%, H: 6.01%, N: 10.44%. Found; C: 71.61%, H: 5.95%, N: 10.56%.

Various methods can be employed to disperse the above described compound represented by the general formula (I) and the above described compound represented by the general formula (II) into a hydrophilic colloid layer. For instance, these compounds can be dissolved in an organic solvent for photographic additives and then the solution can be dispersed in a hydrophilic colloid. Any known organic solvents for photographic additives can be used.

For example, a phthalic acid alkyl ester (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkyl amide (e.g., diethyl laurylamide, etc.), a fatty acid ester (e.g., dibutoxyethyl succinate, dioctyl acetate, etc.), a trimesic acid ester (e.g., tributyl trimesate, etc.), etc. are preferably used. Also, those described in U.S. Pat. Nos. 2,322,027, 2,533,514 and 2,835,579, Japanese Patent Publication No. 23233/71, U.S. Patent 3,287,134, British Pat. No. 958,441, Japanese Patent Application (OPI) No. 1031/72, British Pat. No. 1,222,753, U.S. Pat. No. 3,936,303, Japanese Patent Application (OPI) Nos. 26037/76 and 82078/75, U.S. Pat. Nos. 2,353,262, 2,852,383, 3,554,755, 3,676,137, 3,676,142, 3,700,454, 3,748,141 and 3,837,863, West German patent Application (OLS) No. 2,538,889, Japanese Patent Application (OPI) Nos. 27921/76, 27922/76, 26035/76, 26036/76 and 62632/70, Japanese Patent Publication No. 29461/74, U.S. Pat. Nos. 3,936,303 and 3,748,141, Japanese Patent Application (OPI) No. 1521/78, etc. are preferred. In order to incorporate the magenta coupler and the 1-phenyl-3-pyrazolidone derivative into a hydrophilic colloid layer, the method using the above described organic solvent having a high boiling point as described in U.S. Pat. No. 2,322,027 can be employed, or they are dissolved in an organic solvent having a boiling point of from about 30° to 150° C. such as a lower alkyl acetate (e.g., ethyl acetate, butyl acetate, etc.), ethyl propionate, sec-butyl alcohol, methyl isobutyl ketone, β-ethoxyethyl acetate, methyl cellosolve acetate, etc., and then the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 can also be used.

When a coupler having an acid group, such as a carboxylic acid group, a sulfonic acid group, etc., is used, it can be incorporated in a hydrophilic colloid as an alkaline aqueous solution thereof.

Some techniques which are similar to the present invention are disclosed in Japanese Patent Application (OPI) Nos. 52422/78, 130928/79 and 64339/81. In the technique described in Japanese Patent Application (OPI) No. 52422/78, a 1-phenyl-3-pyrazolidone is incorporated into a color photographic light-sensitive material containing a two-equivalent magenta coupler having a group of —O—Y (wherein Y represents an organic residue) as a split-off group in order to improve the storage stability of the photographic material before exposure to light. However, such a magenta coupler has a low color forming sensitivity and does not form magenta stain which is an issue of the present invention. Therefore, the technique is clearly distinguished from the present invention. Futher, in the present invention, magenta stain can be effectively reduced only when the compound represented by the general formula (II) is used together with the magenta according to the present invention and this is completely unexpected from the technique described in Japanese Patent Application (OPI) No. 52422/78.

The technique described in Japanese Patent Application (OPI) No. 13092/79 does not relate to a 5-pyrazolone magenta coupler but it is concerned with a pyrazole magenta coupler in which the 5-position of the ring is substituted with a sulfonyloxy group or a carbonyloxy group instead of an oxy group. When such a coupler is used together with the compound represented by the general formula (II), the increase in the color forming sensitivity is hardly recognized. In this point of view, the technique is clearly distinguished from the present invention. Also, the presence of such a difference in effect is completely unexpected.

Further, the technique described in Japanese Patent Application (OPI) No. 64339/81 relates to the incorporation of a 1-phenyl-3-pyrazolidone having a substituent represented by the formula R—X—OCH$_2$— on the 4-position thereof in order to accelerate color development. However, when such a compound is used together with the coupler represented by the general formula (I), severe yellow fog is formed and the magenta stain is only prevented to a small extent. On the contrary, the magenta stain can be effectively reduced, only when the compound represented by the general formula (II) is used together with magenta coupler according to the present invention.

The silver halide emulsion used in the present invention can be prepared by using processes described in P. Glafkides, *Chimie et Physique Photographique* (published by Paul Montel Co., 1967); G. F. Duffin, *Photographic Emulsion Chemistry* (published by The Focal Press, 1966); V. L. Zelikman et al., *Making and Coating Photographic Emulsion* (published by The Focal Press, 1964); etc. Any of an acid process, neutral process or ammonia process may be used. Further, a single jet process, a double jet process, or a combination thereof can be used for reacting a soluble silver salt with a soluble halide.

A process for forming particles in the presence of excess silver ion (the so-called reverse mixing process) can be used, too. As one double jet process, it is possible to use a process wherein the liquid phase for forming silver halide is kept at a definite pAg, namely, the so-called controlled double jet process. According to this process, a silver halide emulsion having a regular crystal form and nearly uniform particle size can be obtained.

Two or more silver halide emulsions prepared separately may also be blended.

In the step of formation of the silver halide particles or the step of physical ripening, a cadmium salt, a zinc salt, a lead salt, a thallium salt, an iridium salt or a complex salt thereof, a rhodium salt or a complex salt thereof, an iron salt or a complex salt thereof, etc., may be added thereto.

The photographic emulsion used in the present invention may be spectrally sensitized by methine dyes or others. Examples of dyes used include a cyanine dye, a merocyanine dye, a complex cyanine dye, a complex merocyanine dye, a holopolar cyanine dye, a hemicyanine dye, a styryl dye and a hemioxonol dye. Particularly useful dyes can be selected from the group consisting of a cyanine dye, a merocyanine dye, and complex a merocyanine dye. In these dyes, it is possible to utilize any basic heterocyclic nucleus conventionally utilized for a cyanine dye. Namely, it is possible to utilize a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus and a pyridine nucleus; the above described nuclei to which an alicyclic hydrocarbon ring is fused; and the above described nuclei to which an aromatic hydrocarbon ring is fused, namely, an indolenine nucleus, a benzindolenine nucleus, an indole nucleus, a benzoxalole nucleus, a naphthoxazole nucleus, a benzothiazole nucleus, a naphthothiazole nucleus, a benzoselenazole nucleus, a benzimidazole nucleus, a quinoline nucleus, etc. These nuclei may have substituents on the carbon atoms thereof.

In the merocyanine dye and the complex merocyanine dye, it is possible to utilize, as a nucleus having a ketomethylene structure, a 5- to 6 member heterocyclic nucleus such as a pyrazolin-5-one nucleus, a thiohidantoin nucleus, a 2-thioxazolidin-2,4-dione nucleus, a thiazolidine-2,4-dione nucleus, a rhodanine nucleus, a thiobarbituric acid nucleus, etc.

Examples of useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349, and 4,046,572, British Pat. No. 1,242,588, and Japanese Patent Publication Nos. 14030/69 and 24844/77.

These sensitizing dyes may be used alone, but a combination of them may be used, too. The combination of the sensitizing dyes is frequently used for the purpose of supersensitization. Examples thereof have been described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78 and Japanese Patent Application (OPI) Nos. 110618/77 and 109925/77.

The emulsion may contain a dye which does not have a spectral sensitization function, or a substance showing supersensitization which does not substantially absorb visible rays together with the sensitizing dye. For example, the emulsion may contain an aminostilbene compound substituted with a nitrogen-containing heterocyclic group (for example, those described in U.S. Pat. Nos. 2,933,390 and 3,635,721), an aromatic acid-formaldehyde condensed product (for example, those described in U.S. Pat. No. 3,743,510), a cadmium salt and an azaindene compound. Combinations as described in U.S. Pat. Nos. 3,615,613, 3,615,641, 3,617,295 and 3,635,721 are particularly useful.

For the purpose of increasing sensitivity, increasing contrast, or accelerating development, the photographic emulsion layer of the photographic light-sensitive material of the present invention may contain, for example, polyalkylene oxide or a derivative thereof such as an ether, an ester or an amine, etc., a thioether compound, a thiomorpholine, a quaternary ammonium salt, a urethane derivative, a urea derivative, an imidazole derivative and a 3-pyrazolidone, etc. For example, it is possible to use compounds as described in U.S. Pat. Nos. 2,400,532, 2,423,549, 2,716,062, 3,617,280, 3,772,021 and 3,808,003 and British Pat. No. 1,488,991, etc.

As the binder or protective colloid for the photographic emulsion, gelatin is advantageously used, but other hydrophilic colloids may be used, too.

For example, it is possible to use a protein such as a gelatin derivative, a graft polymer of gelatin with other polymers, albumin, or casein; saccharides, including a cellulose compound such as hydroxyethyl cellulose, carboxymethyl cellulose, cellulose sulfate, etc., sodium alginate, a starch derivative, etc.; and synthetic hydrophilic polymeric substance such as a homopolymer or a copolymer such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc.

As the gelatin, not only lime-processed gelatin, but also acid-processed gelatin, and enzyme-processed gelatin, as described in Bull. Soc. Sci. Phot. Japan, No. 16, page 30 (1966) may be used. Further, a hydrolyzed product and an enzymatic product of gelatin can be used. As the gelatin derivative, it is possible to use those obtained by reacting gelatin with various compounds such as an acid halide, an acid anhydride, an isocyanate, a bromoacetic acid, an alkanesulfone, a vinylsulfonamide, a maleinimide, a polyalkylene oxide, an epoxy compound, etc. Examples thereof have been described in U.S. Pat. Nos. 2,614,928, 3,132,945, 3,186,846 and 3,312,553, British Patent Nos. 861,414, 1,033,189 and 1,005,784, Japanese Patent Publication No. 26845/67, etc.

The above described gelatin graft polymer may be produced by grafting a homopolymer or a copolymer of a vinyl monomer such as acrylic acid, methacrylic acid and a derivative thereof such as an ester or an amide, acrylonitrile, styrene, etc., on gelatin. It is particularly preferred to use a graft polymer of gelatin and a polymer having some degree of compatibility with gelatin, such as a polymer of acrylic acid, methacrylic acid, acrylamide, methacrylamide or hydroxyalkyl methacrylate, etc. Examples thereof have been described in U.S. Pat. Nos. 2,763,625, 2,831,767, 2,956,884, etc.

Examples of typical synthetic hydrophilic polymeric substances include those described in West German Patent Application (OLS) No. 2,312,708, U.S. Pat. Nos. 3,620,751 and 3,879,205, and Japanese Patent Publication No. 7561/68.

The present invention can be applied to a multilayer multicolor photographic light-sensitive material comprising at least two layers having different spectral sensitivities on a support. The multilayer color photographic light-sensitive material generally has at least a red-sensitive emulsion layer, a green-sensitive emulsion layer, and a blue-sensitive emulsion layer on the support. The order of these layers may be suitably varied as occasion demands. Generally, for natural color reproduction, the red-sensitive emulsion layer contains a cyan forming coupler, the green-sensitive emulsion layer contains a magenta forming coupler, and the blue-sensitive emulsion layer contains a yellow forming coupler. However, if desired, other combinations may be utilized.

In the light-sensitive material produced according to the present invention, the hydrophilic colloid layer may contain a water soluble dye as a filter dye or for other purposes such as prevention of irradiation. Examples of such dyes include an oxonol dye, a hemioxonol dye, a styryl dye, a merocyanine dye, a cyanine dye, and an azo dye. Among them an oxonol dye, a hemioxonol dye and a merocyanine dye are particularly useful. Specific examples of such dyes capable of being used include those described in British Pat. Nos. 584,609 and 1,177,429, Japanese Patent Application (OPI) Nos. 85130/73, 99620/74, 114420/74 and 108115/77, and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

In carrying out the present invention, known agents for preventing color fading may be used. Further, such dye image stabilizers in the present invention may be used alone, or two or more of them may be used together. Examples of the known agents for preventing color fading include a hydroquinone derivative as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921, etc., a gallic acid derivative as described in U.S. Pat. Nos. 3,457,079, 3,069,262, etc., p-alkoxyphenol as described in U.S. Pat. Nos. 2,735,765 and 3,698,909, Japanese Patent Publication Nos. 20977/74 and 6623/77, a p-alkoxyphenol derivative as described in U.S. Pat. Nos. 3,432,300, 3,573,050, 3,574,627 and 3,764,337 and Japanese Patent Application (OPI) Nos. 35633/77, 147434/77 and 152225/77, and a bisphenol as described in U.S. Pat. No. 3,700,455.

In the light-sensitive material produced according to the present invention, it is preferred that the hydrophilic colloid layer contain an ultraviolet ray absorbing agent. For example, it is possible to use a benzotriazole compound substituted with an aryl group (for example, those described in U.S. Pat. No. 3,533,794), a 4-thiazolidone compound (for example, those described in U.S. Pat. Nos. 3,314,794 and 3,352,681), a benzophenone compound (for example, those described in Japanese Patent Application (OPI) No. 2784/71, a cinnamic acid ester compound (for example, those described in U.S. Pat. Nos. 3,705,805 and 3,707,375), a butadiene compound (for example, those described in U.S. Pat. No. 4,045,229), and a benzoxazole compound (for example, those described in U.S. Pat. No. 3,700,455). Further, it is possible to use those described in U.S. Pat. No. 3,499,762 and Japanese Patent Application (OPI) No. 48535/79. A coupler having an ultraviolet ray absorbing property (for example, an α-naphthol type cyan dye forming coupler) and a polymer having an ultraviolet ray absorbing property may be used, too. These ultraviolet ray absorbing agents may be mordanted on a sepecified layer.

In the light-sensitive material produced according to the present invention, the photographic emulsion layer and other hydrophilic colloid layers may contain a whitening agent such as a stilbene, triazine, oxazole, or coumarin compound. They may be water soluble. Further, a water insoluble whitening agent may be used in a dispersed state. Specific examples of the fluorescent whitening agents include those described in U.S. Pat. Nos. 2,632,701, 3,269,840 and 3,359,102, British Pat. Nos. 852,075 and 1,319,763, etc.

The light-sensitive material according to the present invention may contain a yellow coupler and/or a cyan coupler in addition to the magenta coupler represented by the general formula (I).

As a yellow coupler, a benzoylacetanilide compound and a pivaloylacetanilide compound are advantageously used. Specific examples of the yellow couplers capable of use include those described in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77, etc.

As a cyan coupler, a phenol compound and a naphthol compound can be used. Specific examples thereof include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 69624/77 and 90932/77, etc.

As a colored coupler, it is possible to use those described, for example, in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, and West German Patent Application (OLS) No. 2,418,959.

As a DIR coupler, it is possible to use those described, for example, in U.S. Pat. Nos. 3,227,554, 3,617,291, 3,701,783, 3,790,384 and 3,632,345, West German Patent Application (OLS) Nos. 2,414,006, 2,454,301 and 2,454,329, British Pat. No. 953,454, Japanese Patent Application (OPI) Nos. 69624/77 and 122335/74 and Japanese Patent Publication No. 16141/76.

In addition to a DIR coupler, the light-sensitive material may contain a compound which releases a development inhibitor at development. For example, those described in U.S. Pat. Nos. 3,297,445 and 3,379,529, West German Patent Application (0LS) No. 2,417,914 and Japanese Patent Application (OPI) Nos. 15271/77 and 9116/78 can be used.

Two or more of the above described couplers may be contained in the same layer. Two or more layers may contain the same compound.

These couplers are added generally in an amount of from $2 \times 10^{-3}$ mols to $5 \times 10^{-1}$ mols, and preferably from $1 \times 10^{-2}$ mols to $5 \times 10^{-1}$ mols per mol of silver in the emulsion layer.

The photographic processing of the light-sensitive material of the present invention can be carried out by any known process. Know processing solutions can be used. The processing temperature is selected, generally, from 18° C. to 50° C., but a temperature of lower than 18° C. or higher than 50° C. may be used.

The color developing solution is generally composed of an alkaline aqueous solution containing a color developing agent. As the color developing agent, known primary aromatic amine developing agent can be used, examples of which include a phenylenediamine (for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline, etc.).

In addition, those described in L. F. A. Mason, *Photographic Processing Chemistry* (Focal Press, 1966) pages 226–229, U.S. Pat. Nos. 2,193,015 and 2,592,364, and Japanese Patent Application (OPI) No. 64933/73 may be used.

The color developing solution may contain a pH buffer agent such as a sulfite, a carbonate, a borate or a phosphate of an alkali metal, and a development restrainer or an antifogging agent such as a bromide, an iodide, an organic antifogging agent, etc. If necessary, it may contain a water softener, a preservative such as hydroxylamine, an organic solvent such as benzyl alcohol or diethylene glycol, a development accelerator such as polyethylene glycol, a quaternary ammonium salt or an amine, a dye forming coupler, a competitive coupler, a fogging agent such as sodium borohydride, an auxiliary developing agent such as 1-phenyl-3-pyrazolidone, a thickener, a polycarboxylic acid type chelating agent as described in U.S. Pat. No. 4,083,723, and an antioxidant as described in West German Patent Application (OLS) No. 2,622,950, etc.

After carrying out the color development, the photographic emulsion layers are generally subjected to bleaching. The bleaching may be carried out simultaneously with fixing or may be carried out separately. As the bleaching agent, a compound of a polyvalent metal such as iron (III), cobalt (III), chromium (VI) or copper (II), etc., a peracid, a quinone, a nitroso compound, etc., can be used. For example, it is possible to use a ferricyanide, a bichromate, and an organic complex salt of iron (III) or cobalt (III), for example, a complex salt of an aminopolycarboxylic acid such as ethylenediaminetetraacetic acid, nitrilotriacetic acid or 1,3-diamino-2-propanol tetraacetic acid, etc., or an organic acid such as citric acid, tartaric acid, malic acid, etc.; a persulfate; a permanganate; nitrosophenol; etc. Among them, potassium ferricyanide, (ethylenediaminetetraacetato)iron (III) sodium complex and (ethylenediaminetetraacetato)iron (III) ammonium complex are particularly useful. (Ethylenediaminetetraacetato)iron (III) complexes are useful for both a bleaching solution and a mono-bath bleach-fix solution.

To the bleaching solution or the bleach-fix solution, it is possible to add a bleaching accelerator as described in U.S. Pat. Nos. 3,042,520 and 3,241,966, and Japanese Patent Publication Nos. 8506/70 and 8836/70, a thiol compound as described in Japanese Patent Application (OPI) No. 65732/78, and various other additives.

The light-sensitive material according to the present invention are preferably processed with the developing solution supplemented or controlled by the methods as described in Japanese Patent Application (OPI) Nos. 84636/76, 119934/77, 46732/78, 9626/79, 19741/79, 37731/79, Japanese Patent Application Nos. 76158/79, 76159/79 and 102962/79, etc.

The bleach-fix solution used for processing the light-sensitive material according to the present invention is preferably that which is regenerated by the processes as described in Japanese Patent Application (OPI) Nos. 781/71, 49437/73, 18191/73, 145231/75, 18541/76, 19535/76 and 144620/76 and Japanese Patent Publication No. 23178/76, etc.

The present invention is illustrated in greater detail by reference to the following examples, but the present invention is not to be construed as being limited thereto.

EXAMPLE 1

On a transparent cellulose triacetate support, was coated a coating solution having the composition described below and on this emulsion layer was coated a gelatin protective layer (coating amount of gelatin: 1 g/m$^2$) to prepare samples A to N.

COMPOSITION OF COATING SOLUTION

Green-sensitive silver iodobromide emulsion (silver iodide: 6 mol%, silver bromide: 94 mol%, coating amount of silver: 1 g/m$^2$)

Coating amount of magenta coupler: $7 \times 10^{-4}$ mol/m$^2$

Compound added according to the present invention as shown in Table 1 below: $7 \times 10^{-5}$ mol/m$^2$

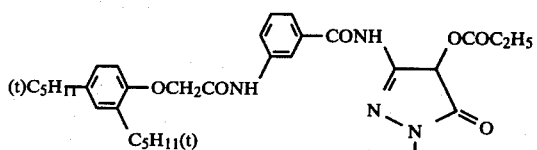

COMPARISON COUPLER—2

Compound described in Japanese Patent Application (OPI) No. 52422/78.

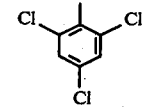

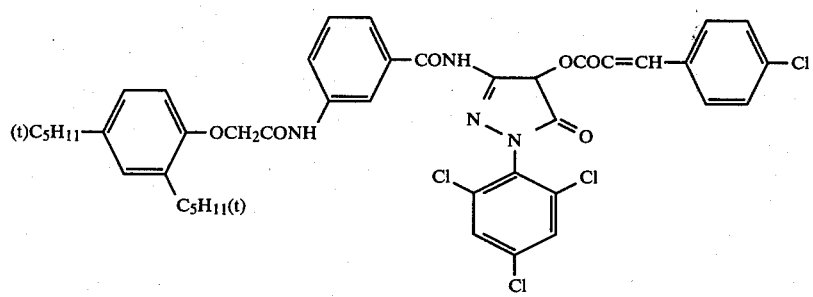

Solvent for dispersing coupler: Tricresyl phosphate

TABLE 1

| Sample | Magenta Coupler | Compound Added |
|---|---|---|
| A | I - 3 | II - 1 |
| B | I - 3 | II - 21 |
| C | I - 5 | II - 2 |
| D | I - 5 | II - 21 |
| E | I - 15 | II - 1 |
| F | I - 15 | II - 37 |
| G | I - 15 | Comparison Compound - 1 |
| H | I - 29 | II - 3 |
| I | I - 29 | II - 22 |
| J | I - 29 | Comparison Compound - 2 |
| K | Comparison Coupler - 1 | II - 21 |
| L | Comparison Coupler - 2 | Comparison Compound - 2 |
| M | Comparison Coupler - 3 | II - 21 |
| N | Comparison Coupler - 4 | II - 21 |

COMPARISON COUPLER—1

Compound described in Japanese Patent Application (OPI) No. 52422/78.

COMPARISON COUPLER—4

Four-equivalent coupler

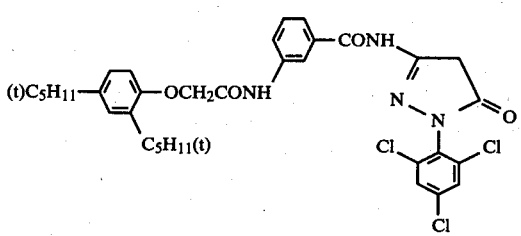

COMPARISON COMPOUND—1

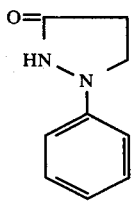

COMPARISON COMPOUND—2

Compound described in Japenese Patent Application (OPI) No. 64339/81.

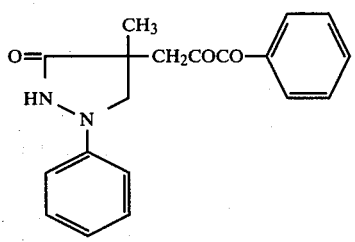

In addition to the above described samples, 14 kinds of samples were prepared in the same manner as described above except that the 1-phenyl-3-pyrazolidone compound was not added to the composition of coating solution. These samples were designated Samples A' to N', which corresponded to Samples A to N, respectively.

These samples were exposed to light through an optical wedge and then subjected to the following processing steps:

| Processing Step | Temperature (°C.) | Time |
|---|---|---|
| 1. Color development | 38 | 3 min 15 sec |
| 2. Bleaching | " | 6 min 30 sec |
| 3. Washing with water | " | 2 min |
| 4. Fixing | " | 4 min |
| 5. Washing with water | " | 4 min |
| 6. Stabilizing bath | " | 1 min |

The processing solutions used had the following compositions:

| Color Developer Solution | |
|---|---|
| 4-Amino-3-methyl-N—ethyl-N—($\beta$-hydroxyethyl)aniline Monosulfate | 5 g |
| Sodium Sulfite | 5 g |
| Hydroxylamine Sulfate | 2 g |
| Postassium Carbonate | 30 g |
| Potassium Hydrogen Carbonate | 1.2 g |
| Potassium Bromide | 1.2 g |
| Sodium Chloride | 0.2 g |
| Trisodium Nitrilotriacetate | 1.2 g |
| 10% $H_2SO_4$ to adjust pH to 10.1 | |
| Water to make | 1,000 ml |
| Bleaching Solution | |
| Iron (III) Ammonium Ethylenediaminetetraacetate | 100 g |
| Disodium Ethylenediaminetetraacetate | 10 g |
| Potassium Bromide | 150 g |
| Glacial Acetic Acid | 10 g |
| Aqueous Ammonia to adjust pH to 6.0 | |
| Water to make | 1,000 ml |

| -continued | |
|---|---|
| Fixing Solution | |
| Ammonium Thiosulfate | 150 g |
| Sodium Sulfite | 10 g |
| Sodium Hydrogen Sulfite | 2.5 g |
| 10% $H_2SO_4$ to adjust pH to 6.0 | |
| Water to make | 1,000 ml |
| Stabilizing Bath | |
| Formalin (37%) | 5 ml |
| Fuji Drywell (Surfactant: Produced by Fuji Photo Film Co., Ltd.) | 3 ml |
| Water to make | 1,000 ml |

The optical density of the samples thus processed was measured using green light. Fog value and sensitivity by an ASA sensitivity indicating method were obtained and the rate of sensitivity was calculated. The results thus obtained are shown in Table 2 below.

TABLE 2

| Magenta Fog Density | | Rate of Sensitivity |
|---|---|---|
| A | 0.10 | |
| A' | 0.25 | A/A' = 1.36 |
| B | 0.11 | |
| B' | 0.25 | B/B' = 1.34 |
| C | 0.12 | |
| C' | 0.27 | C/C' = 1.40 |
| D | 0.12 | |
| D' | 0.27 | D/D' = 1.41 |
| E | 0.11 | |
| E' | 0.30 | E/E' = 1.39 |
| F | 0.13 | |
| F' | 0.30 | F/F' = 1.38 |
| G | 0.25 | |
| G' | 0.30 | G/G' = 0.88 |
| H | 0.09 | |
| H' | 0.21 | H/H' = 1.42 |
| I | 0.10 | |
| I' | 0.21 | I/I' = 1.30 |
| J | 0.18 | |
| J' | 0.21 | J/J' = 1.01 |
| K | 0.13 | |
| K' | 0.14 | K/K' = 1.00 |
| L | 0.12 | |
| L' | 0.13 | L/L' = 0.98 |
| M | 0.13 | |
| M' | 0.14 | M/M' = 1.05 |
| N | 0.10 | |
| N' | 0.10 | N/N' = 1.04 |

From the results as shown in Table 2 above, it is apparent that the 1-phenyl-3-pyrazolidone compounds according to the present invention can prevent magenta fog of the two-equivalent magenta coupler represented by the general formula (I) and further, show a sufficient sensitivity increasing effect. On the contrary, the fog preventing effect is small and the sensitivity increasing effect is not observed when Comparison Compounds—1 and —2 are used. In particular, when Comparison Compound—2 is used, a large yellow fog is observed. On the other hand, the sensitivity increasing effect is ot observed while the magenta stain is small, when Comparison Couplers 1 to 4 are used.

EXAMPLE 2

On a polyethylene-laminated paper support, were coated, in the order, a dispersion prepared by dispersing α-pivaloyl-α-[4-(4-benzyloxysulfonyl)phenoxy]-2-chloro-5-[γ-(2,4-di-tert-amylphenoxy)-butyramido]acetanilide (Yellow Coupler) dissolved in dioctyl butyl phosphate in a silver chlorobromide emulsion (silver bromide, 80 mol%) (silver: 0.4 g/m$^2$; coupler: $8 \times 10^{-4}$ mol/m$^2$; oil for coupler: 0.3 g/m$^2$); a gelatin intermediate layer (gelatin: 1 g/m$^2$); an emulsion prepared by emulsifying the magenta coupler and the 1-phenyl-3-pyrazolidone compound according to the present invention as described in Table 3 below dissolved in tricresyl phosphate in a silver chlorobromide emulsion (silver bromide, 60 mol%) (silver: 0.23 g/m$^2$; coupler: $5.8 \times 10^{-4}$ mol/m$^2$; compound: $7 \times 10^{-5}$ mol/m$^2$; oil for coupler: 0.35 g/m$^2$); a gelatin intermediate layer containing a solvent (gelatin: 1.2 g/m$^2$; dibutyl phthalate: 0.25 g/m$^2$; 2-(2-hydroxy-3-sec-butyl-5-tert-butylphenyl)benzotriazole: 1 g/m$^2$); an emulsion prepared by emulsifying 1-hydroxy-4-chloro-2-n-dodecyl-naphthamide (cyan coupler) dissolved in dibutyl phthalate in a silver chlorobromide emulsion (silver bromide, 50 mol%) (silver 0.3 g/m$^2$; coupler: $8.5 \times 10^{-4}$ mol/m$^2$; oil for coupler 0.2 g/m$^2$); and finally a gelatin protective layer (gelatin: 1 g/m$^2$) to prepare Samples O to Z.

TABLE 3

| Sample | Magenta Coupler | Compound Added |
|---|---|---|
| O | I - 1 | II - 1 |
| P | I - 1 | II - 2 |
| Q | I - 5 | II - 1 |
| R | I - 5 | II - 2 |
| S | I - 5 | Comparison Compound - 1 |
| T | I - 29 | II - 32 |
| U | I - 29 | II - 41 |
| V | I - 29 | Comparison Compound - 2 |
| W | Comparison Coupler - 1 | II - 32 |
| X | Comparison Coupler - 2 | II - 32 |
| Y | Comparison Coupler - 3 | II - 32 |
| Z | Comparison Coupler - 4 | II - 32 |

In addition to the above described samples, 12 kinds of samples were prepared in the same manner as described above except that the 1-phenyl-3-pyrazolidone compound was not added to the composition of the coating solution. These samples were designated Samples O' to Z', which corresponded to Samples O to Z, respectively.

These samples were exposed to light through an optical wedge and processed according to the following steps:

| Processing Step (33° C.) | |
|---|---|
| Color development | 3 min 30 sec |
| Bleach-fixing | 1 min 30 sec |
| Washing with water | 2 min |
| Drying | 10 min |

The composition of each processing solution is set forth below:

| Color Developer Solution | |
|---|---|
| Benzyl Alcohol | 10 ml |
| Diethylene Glycol | 3 ml |
| Potassium Carbonate | 25 g |
| Sodium Chloride | 0.1 g |
| Sodium Bromide | 0.5 g |
| Anhydrous Sodium sulfite | 2 g |
| Hydroxyamine Sulfate | 2 g |
| N—Ethyl-N—β-methanesulfonamidoethyl-3-methyl-4-aminoaniline sulfate | 4 g |
| Water to make | 1 l |
| Sodium hydroxide (NaOH) was added to adjust the pH to 10. | |
| Bleach-Fixing Solution | |
| Ammonium Thiosulfate | 124.5 g |
| Sodium Metabisulfite | 13.3 g |
| Anhydrous Sodium Sulfite | 2.7 g |
| Iron (III) Ammonium Ethylene-diaminetetraacetate | 65 g |
| Color Develope Solution (as described above) | 100 ml |
| Adjustment of pH to 6.7 to 6.8 using 10% $H_2SO_4$ | |
| Water to make | 1 l |

The magenta density of the samples processed was measured using a Macbeth densitometer. Fog value and sensitivity by an ASA sensitivity indicating method were obtained and the rate of sensitivity was calculated. The results thus obtained are shown in Table 4 below.

TABLE 4

| Magenta Fog Density | | Rate of Sensitivity |
|---|---|---|
| O | 0.18 | O/O' = 1.40 |
| O' | 0.35 | |
| P | 0.17 | P/P' = 1.36 |
| P' | 0.36 | |
| Q | 0.16 | Q/Q' = 1.37 |
| Q' | 0.40 | |
| R | 0.17 | R/R' = 1.36 |
| R' | 0.40 | |
| S | 0.35 | S/S' = 0.95 |
| S' | 0.41 | |
| T | 0.17 | T/T' = 1.41 |
| T' | 0.37 | |
| U | 0.16 | U/U' = 1.40 |
| U' | 0.37 | |
| V | 0.30 | V/V' = 1.01 |
| V' | 0.37 | |
| W | 0.18 | W/W' = 1.01 |
| W' | 0.20 | |
| X | 0.16 | X/X' = 0.98 |
| X' | 0.16 | |
| Y | 0.17 | Y/Y' = 1.02 |
| Y' | 0.18 | |
| Z | 0.18 | Z/Z' = 1.00 |
| Z' | 0.18 | |

From the results as shown in Table 4 above, it is apparent that when the compound represented by the general formula (II) is used in combination with the two-equivalent coupler according to the present invention, the formation of magenta stain is prevented and further, the sensitivity increasing effect is observed. On the contrary, when Comparison Couplers 1 to 4 or Comparison Compounds 1 to 2 are used, the above described effect is not obtained.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon a silver halide emulsion layer containing at least one coupler represented by the following general formula (I):

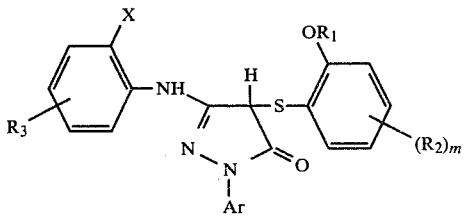

wherein $R_1$ represents an alkyl group or an aryl group; $R_2$ represent a hydrogen atom, a hydroxy group, a halogen atom, an alkyl group, an alkoxy group or an aryl group; $R_3$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trichloromethyl group; X represents a halogen atom or an alkoxy group; Ar represents a substituted phenyl group; m is an integer of from 1 to 4; and the above described organic groups may be substituted; and the silver halide emulsion layer and/or a hydrophilic colloid layer adjacent thereto containing a 1-phenyl-3-pyrazolidone derivative represented by the the following general formula (II):

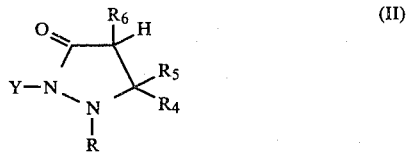

wherein Y represents a hydrogen atom or an acyl group; R and $R_4$, which may be the same or different, each represents an aryl group; $R_5$ represents a hydrogen atom or an alkyl group; $R_6$ represents a hydrogen atom, an alkyl group or an aryl group; and the above described organic groups may be substituted.

2. A silver halide color photographic light-sensitive material as claimed in claim 1, wherein the substituent for the substituted phenyl group represented by Ar is a halogen atom, an alkyl group having from 1 to 22 carbon atoms, an alkoxy group having from 1 to 22 carbon atoms, an alkoxycarbonyl group having from 2 to 23 carbon atoms or a cyano group.

3. A silver halide color photographic light-sensitive material as claimed in claim 1, wherein the alkoxy group represented by X is an alkoxy group having from 1 to 22 carbon atoms.

4. A silver halide color photographic light-sensitive material as claimed in claim 1, wherein the group $R_3$ includes an alkyl moiety having from 1 to 36 carbon atoms.

5. A silver halide color photographic light-sensitive material as claimed in claim 1, wherein the group $R_3$ includes an aryl moiety having from 6 to 38 carbon atoms.

6. A silver halide color photographic light-sensitive material as claimed in claim 1, wherein the alkyl group represented by $R_1$ is an alkyl group having from 1 to 22 carbon atoms.

7. A silver halide color photographic light-sensitive material as claimed in claim 1, wherein the aryl group represented by $R_1$ is an aryl group having from 1 to 18 carbon atoms.

8. A silver halide color photographic light-sensitive material as claimed in claim 1, wherein the total number of carbon atoms included in the groups represented by $R_1$ and $R_2$ is not less than 6.

9. A silver halide color photographic light-sensitive material as claimed in claim 1, wherein the acyl group represented by Y is an acyl group having 2 to 15 carbon atoms.

10. A silver halide color photographic light-sensitive material as claimed in claim 1, wherein the aryl group represented by R is an aryl group having from 6 to 15 carbon atoms.

11. A silver halide color photographic light-sensitive material as claimed in claim 1, wherein the aryl group represented by $R_4$ is an aryl group having from 6 to 30 carbon atoms.

12. A silver halide color photographic light-sensitive material as claimed in claim 1, wherein the alkyl group represented by $R_5$ is an alkyl group having from 1 to 12 carbon atoms.

13. A silver halide color photographic light-sensitive material as claimed in claim 1, wherein the alkyl group represented by $R_6$ is an alkyl group having from 1 to 10 carbon atoms.

14. A silver halide color photographic light-sensitive material as claimed in claim 1, wherein the aryl group represented by $R_6$ is an aryl group having from 6 to 30 carbon atoms.

15. A silver halide color photographic light-sensitive material as claimed in claim 1, wherein the coupler represented by the general formula (I) is present in an amount of from $1 \times 10^{-5}$ to $1 \times 10^{-2}$ g/m$^2$.

16. A silver halide color photographic light-sensitive material as claimed in claim 1, wherein the 1-phenyl-3-pyrazolidone derivative represented by the general formula (II) is present in an amount of from $1 \times 10^{-6}$ to $1 \times 10^{-2}$ 8/m$^2$.

17. A silver halide color photographic light-sensitive material as claimed in claim 1, wherein the 1-phenyl-3-pyrazolidone derivative represented by the general formula (II) is present in the silver halide emulsion layer.

18. A silver halide color photographic light-sensitive material as claimed in claim 1, wherein the silver halide emulsion layer is a green-sensitive silver halide emulsion layer.

19. A silver halide color photographic light-sensitive material as in claim 18, wherein the photographic material further contains a blue-sensitive silver halide emulsion layer containing a yellow color-forming coupler and a red-sensitive silver halide emulsion layer containing a cyan color-forming coupler.

20. A method of forming a color image comprising developing an imagewise exposed silver halide color photographic light-sensitive material comprising a support having thereon a silver halide emulsion layer containing at least one coupler represented by the following general formula (I):

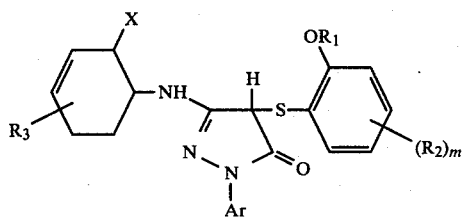

wherein $R_1$ represents an alkyl group or an aryl group; $R_2$ represent a hydrogen atom, a hydroxy group, a halogen atom, an alkyl group, an alkoxy group or an aryl group; $R_3$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trichloromethyl group; X represents a halogen atom or an alkoxy group; Ar represents a substituted phenyl group; m is an integer of from 1 to 4; and the above described organic groups may be substituted; and the silver halide emulsion layer and/or a hydrophilic colloid layer adjacent thereto containing a 1-phenyl-3-pyrazolidone derivative represented by the following general formula (II):

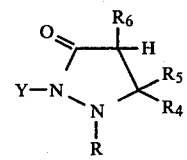

wherein Y represents a hydrogen atom or an acyl group; R and $R_4$, which may be the same or different, each represents an aryl group; $R_5$ represents a hydrogen atom or an alkyl group; $R_6$ represents a hydrogen atom, an alkyl group or an aryl group; and the above described organic groups may be substituted.

21. A silver halide color photographic light-sensitive material as claimed in claim 1, wherein the amount of Ag in the silver halide emulsion layer is from 0.1 to 10 g/m².

22. A silver halide color photographic light-sensitive material as claimed in claim 1, wherein the amount of the compound represented by the general formula (II) is from $1 \times 10^{-3}$ to 1 mole per mole of silver in the silver halide emulsion layer.

* * * * *